United States Patent
Langen et al.

(12) 
(10) Patent No.: US 6,358,220 B1
(45) Date of Patent: Mar. 19, 2002

(54) THERMOPLASTIC CASTING MATERIAL AND METHOD FOR PRODUCTION THEREOF

(75) Inventors: Gunter Langen, Wolfstein; Marita Meister; Joachim Burger, both of Kaiserslautern, all of (DE)

(73) Assignee: Karl Otto Braun KG, Wolfstein (DE)

( * ) Notice: Subject to any disclaimer, the term of this patent is extended or adjusted under 35 U.S.C. 154(b) by 0 days.

(21) Appl. No.: 09/504,858

(22) Filed: Feb. 16, 2000

(30) Foreign Application Priority Data

Feb. 19, 1999 (DE) .......................... 199 07 043

(51) Int. Cl.[7] ................................ A61F 5/00
(52) U.S. Cl. .................... 602/8; 602/5; 602/6
(58) Field of Search ................ 602/6–11; 442/306, 442/312, 313, 164, 180, 103; 428/902, 903

(56) References Cited

U.S. PATENT DOCUMENTS

| | | |
|---|---|---|
| 3,420,231 A | 1/1969 | Edenbaum |
| 4,105,025 A | 8/1978 | Wang et al. |
| 4,143,655 A | 3/1979 | Custer et al. |
| 4,226,230 A | 10/1980 | Potts |
| 4,454,873 A | 6/1984 | Laufenberg |
| 4,473,671 A | 9/1984 | Green |
| 4,522,203 A | 6/1985 | Mays |
| 4,882,230 A * | 11/1989 | Warner .................... 428/516 |

FOREIGN PATENT DOCUMENTS

| | | |
|---|---|---|
| DE | 40 33 633 A1 | 5/1991 |
| DE | 40 31 942 A1 | 4/1992 |
| DE | 40 31 943 A1 | 4/1992 |
| DE | 40 38 705 A1 | 6/1992 |
| EP | 0 006 263 A1 | 1/1980 |
| EP | 0 446 431 A2 | 9/1991 |
| EP | 0 658 124 B1 | 6/1997 |
| WO | WO 90/14060 | 11/1990 |
| WO | WO 93/07194 | 4/1993 |
| WO | WO 94/03211 | 2/1994 |
| WO | WO 94/05339 | 3/1994 |
| WO | WO 95/13039 | 5/1995 |
| WO | WO 95/19751 | 7/1995 |
| WO | WO 95/26698 | 10/1995 |
| WO | WO 96/19346 | 6/1996 |
| WO | WO 96/40028 | 12/1996 |
| WO | WO 97/29909 | 8/1997 |

* cited by examiner

Primary Examiner—Michael A. Brown
Assistant Examiner—Lalita M. Hamilton
(74) Attorney, Agent, or Firm—Nath & Associates PLLC; Gary M. Nath; Marvin C. Berkowitz

(57) ABSTRACT

The invention relates to a thermoplastic casting material, especially a thermoplastic casting material for orthopedic and other medical applications for immobilization of extremities and/or joints, that comprise a first textile fabric, a thermoplastic polymer applied to the first textile fabric and at least one second textile fabric applied to this composite.

Figure 1:
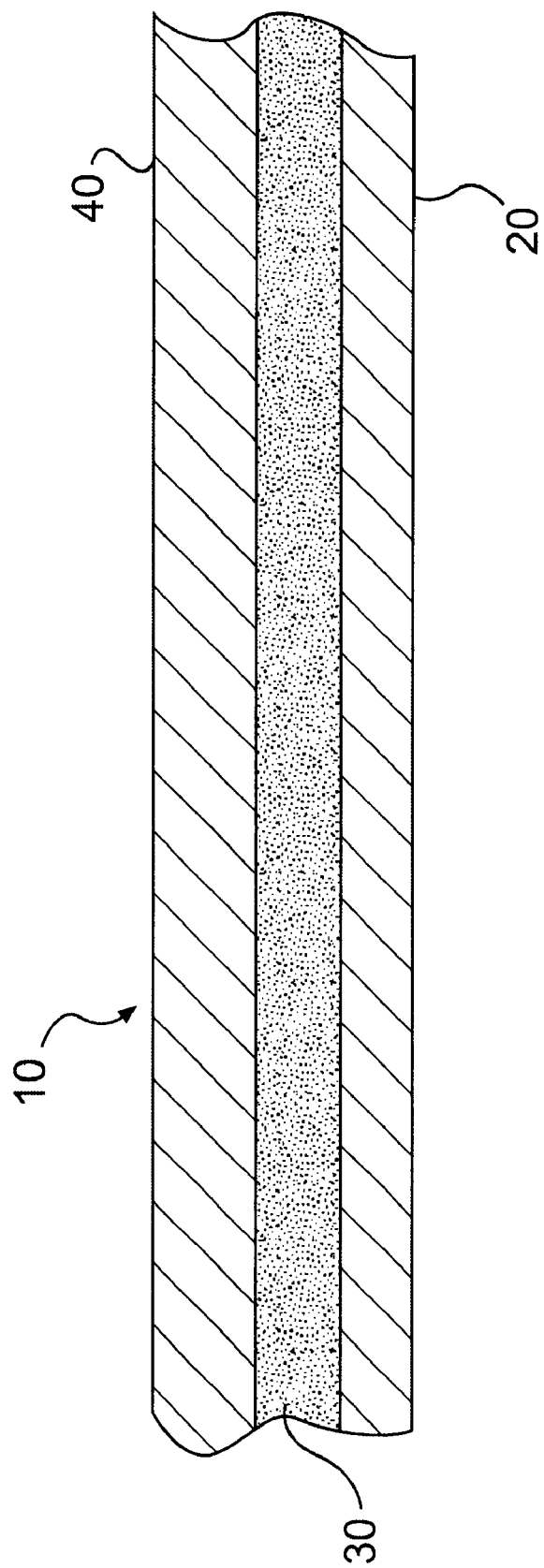

Additionally, the invention relates to a method for the production of this thermoplastic casting material that comprises the following steps:

a) application of a thermoplastic polymer on a first textile fabric and b) application of at least one second textile fabric on the first textile fabric from step a) provided with the thermoplastic polymer.

14 Claims, 1 Drawing Sheet

THERMOPLASTIC CASTING MATERIAL AND METHOD FOR PRODUCTION THEREOF

The invention relates to a thermoplastic casting material, especially a thermoplastic casting material in roll form, preferably for orthopedic and other medical applications for immobilization of extremities and/or joints. Additionally, the invention relates to a method for the production of this thermoplastic casting material.

Alternative casting materials based on synthetic polymers have been known for some time in addition to the customary plaster of paris cast materials used for a long time. These possess the advantages compared to plaster of paris casts that they have improved mechanical properties, that they are unaffected by water and, as a consequence, are washable, and ensure an increased wearing comfort and better mobility as a result of their rapid applicability and hardening and due to their light weight. Furthermore, in contrast to plaster materials, casting systems based on synthetic polymers are translucent to x-ray radiation and thus allow x-ray follow-up examinations without having to remove the casting.

Plaster of paris as well as the casting materials based on plastic are essentially composed of an organic or inorganic textile supporting material and the plaster and/or synthetic polymer material applied thereto. With plastic materials, a differentiation is to be made between irreversibly hardenable materials and thermoplastic, reversibly moldable materials.

Among the irreversibly hardenable synthetic polymer casting materials, water-hardening systems have primarily prevailed that contain reactive polyurethane prepolymers as hardenable synthetic polymer components which harden through contact with water. By suitably choosing the formulation, casting materials can be attained that, after dipping in water, harden within a time period that allows the professional application and modeling of the casting material to the human or animal body. As long as the synthetic polymer is not hardened, the individual layers of the casting material are capable of sticking to each other whereby a cast comprising several layers of the casting material is finally obtained.

With thermoplastic, reversibly moldable casting materials, the self-adhesive characteristic is achieved by heating the thermoplastic polymer to or above the respective softening temperature. The material hardens again upon cooling, whereby it remains pliable and capable of being modeled for some time at temperature below the melting point. A multi-layered self-bound casting system is obtained after the hardening of the thermoplastic resin.

Although they dominate the market at the present time, the hardenable synthetic polymer casting materials, i.e. water-hardenable casting materials based on polyurethane resins, are disadvantageous in comparison to thermoplastic systems. A moisture-free production and a complicated packaging of the product that is impermeable to water and air is necessary as a result of the desired property of water-hardenability. Additionally, the water-hardenable resin formulations are complex and correspondingly expensive. By maintaining conditions which are as moisture-free as possible, the storage stability of approximately 24 months is also low. Additionally, the isocyanates contained in the polyurethane resins are sensitizing, irritating and damaging to health and, as a result, are not without risk in use with high-risk patients.

A problem inherent to the hardenable as well as the thermoplastic casting materials is that an adhesion of the layers at the position of application is desired and necessary, but on the other hand, an adhesion of the layers at a point in time other then during the direct application must be avoided.

Thus, WO 95/19751 describes an orthopedic casting material of a support fabric and a material applied thereto of a hardenable resin and a filler bound thereto. In order to prevent the individual layers of the casting material from sticking together during storage, a volatile, water-soluble liner is applied to the material as a separator. This liner is dissolved and removed when the casting material equipped with the water-hardenable resin is brought into contact with water to initialize hardening.

A thermoplastic casting material is described in U.S. Pat. No. 4,445,873. It consists of a flexible fabric substrate, typically of a knitted cotton material, and is coated with a polyester resin. This coated material remains flexible and can be stored in the form of rolls. In order that the individual layers of the material do not adhere to each other when softening the resin in hot water before they are applied to the desired location on the body, a polyethylene oxide layer is applied to the resin/support composite. This layer dissolves upon softening in water and thus releases the self-adhering surface of the thermoplastic resin.

In U.S. Pat. No. 3,420,231 a casting material consisting of a substrate and a thermoplastic resin is described as known which is present in rolled-up form and has a separation material to prevent the adhesion of neighboring layers, for example a paper interlining. This arrangement is regarded as unsatisfactory and U.S. Pat. No. 3,420,231 proposes to replace the interliner to be removed before application with a coating of a water-soluble resin with inverse solubility in water. As a result of the inverse solubility, the interlayers are not dissolved when heating and softening of the thermoplastic resin in hot water. After application of the casting material, the protective layer dissolves in the adhering, now cooled residual water and allows adhesion of the individual layers.

Finally, U.S. Pat. No. 4,143,655 discloses an orthopedic casting material that is constructed of a textile substrate and a thermoplastic polymer applied thereto. A polyethylene film mesh is applied to one side of the coated substrate as a separation layer for preventing the adhesion of neighboring layers. As a result, adhesion of the layers is prevented when heating the casting material. Upon application of the casting material, the polyethylene film is pulled off and an adhesion of the individual layers with each other is thus made possible.

The measures described above for preventing the undesired adhesion of hardenable or thermoplastic polymer casting materials brings about a certain improvement in comparison to completely unprotected casting material systems, but are however still unsatisfactory and not suitable to prevent an undesired adhesion of the casting material with certainty.

Thus, when using a water-soluble separator, the protective effect is already lost in the water bath into which the casting material is brought to the required temperature for softening the thermoplastic polymer or for initializing the hardening of the water-hardenable synthetic polymer. Hence, the possibility exists that an adhesion of the neighboring layers of the casting material which are present for the most part in rolled up form, occurs after removal from the water bath or already in the water bath.

Furthermore, the use of a water-soluble or inverse water-soluble protective film is connected with the limitation that a water bath must be used for heating the material. Heating, for example, via hot air blower or in an oven is not possible.

The use of interlinings that are to be removed before application is unsatisfactory because handling is clearly made more difficult by the separation of the material at the moment of use and, furthermore, unnecessary waste is created. Consequently, the object of the invention was to develop a thermoplastic casting material that allows good adhesion of the neighboring casting material layers upon application but effectively prevents adhesion of the layers up to this time point without the use of a separator such that the material can be easily unrolled and is easy to handle and does not lead to the creation of waste or to the contamination of the water bath used.

Furthermore, a method is to be made available that allows the production of such a casting material in a simple and inexpensive manner.

The above problems could be solved according to the invention, a first embodiment of which is shown in FIG. 1, by making available a thermoplastic casting material that comprises a thermoplastic casting material (cast bandage) 10 that comprises a first textile fabric 20, a thermoplastic polymer 30 applied to the first textile fabric and at least one second textile fabric 40 applied to this composite as defined in the claims as well by the method for production thereof as also defined in the claims.

An adhesive bond between the above mentioned components is created amongst each other in the production or, at the latest, upon heating the casting material. As a result, a composite is created from the first textile fabric provided with the thermoplastic polymer and the at least one second textile fabric adhering thereon that can then be processed under retention of all components into the resulting cast.

As a result of this surprising solution, a new thermoplastic casting material is made available that not only represents a subtile distinction and further development of the prior art but considerable extends this through the following advantages:

- the heated cast bandage is capable of being unrolled extremely easily, even after strongly squeezing out the residual water after heating in a water bath.
- the second textile fabric does not disadvantageously influence the adhesion of the layers.
- the second textile fabric remaining in the finished cast contributes to an increase of the stability and to the improvement of the air permeability of the cast at the same time.
- the casting material can be employed after heating without having to remove a adhesion protective layer. As a result, the handling upon application of the casting material is clearly improved and contamination of the water bath used for heating does not occur.
- the second fabric, oriented to the outside upon application of the casting material, lies on the casting material surface whereby a textile surface character of the casting material is brought about and, therewith, an increased wearing comfort.

In the following, the thermoplastic casting material as well as the method for production thereof is described in detail and further illustrated by means of concrete examples.

The casting material according to the invention comprises at least a first textile fabric, a thermoplastic polymer applied to the first textile fabric and a second textile fabric applied to this composite.

The first textile fabric is a woven fabric, a non-woven fabric or a warp knitted or knitted textile fabric, preferably a warp knitted first textile fabric, more preferably a warp knitted fabric with open-pore structure.

Particularly preferred is a first textile fabric that has expandable and/or elastic properties.

The term "expandable" used in various passages herein is to be understood such that it includes inelastic and elastic expandability where it is technically sensible.

Synthetic, regenerated and natural fibers as well as mixtures thereof are useable as fiber and/or thread materials. Textile materials of mixtures of elastic and inelastic fibers and/or threads are produced for attaining the particularly advantageous elastic first textile fabric.

Non-elastic fibers and/or threads for the first textile fabric are, for example, cotton, viscose as well as synthetic fibers and/or threads such as, for example, polyacrylic, polyamide, aramide, polyester, polyolefins or inorganic fiber materials such as, for example, glass fibers or carbon fibers.

Elastic fiber and/or thread elements are, for example, yarns of elastodiene, thermoplastic elastomers, elastane, elastic polyamide or polyurethane fibers, texturized synthetic yarns, highly twisted single threads or highly twisted double threads made from cotton or viscose fibers.

The elastic as well as the non-elastic fibers and/or threads can be used in different thickness as a function of the thickness of the desired support material and/or end product. With non-wovens, the fiber thickness preferably lies at 0.01-1 tex. With warp knitted, knitted and woven fabrics, the thread thickness of the non-elastic threads normally lies at a thread denier of 4-200 tex (tex=unit of measure of the thread denier in g/1,000 m), preferably 10-110 tex, most preferred 20-60 tex.

The thread denier of the elastic threads is preferably somewhat lower and lies at 4-80 tex, preferably 10-40 tex, most preferred 15-30 tex.

The first textile fabric can comprise one or more different types of fibers and/or threads that differ from each other with respect to the material and/or the yarn thickness. It can contain one or more types of non-elastic yarns and is, in as far as it is present, one or more types of elastic yarns.

Particularly preferred are elastic first textile fabrics of synthetic threads and/or fibers of one or more synthetic materials, for example, polyester fibers or polyamide threads as non-elastic yarns and polyurethane threads and/or fibers as elastic yarns.

As already stated, the first textile fabric is preferably expandable/elastic in length-wise as well as crosswise direction independent of its textile manner of production (warp knitted, woven, non-woven or knitted). The length-wise direction characterizes the machine-direction of the fabric and the crosswise direction characterizes the direction perpendicular to this that defines the width of the first textile fabric.

The length-wise expandability is preferably from 30–200%, more preferably 60–110%, most preferably 85–100%.

The crosswise expandability is preferably from 10–120%, more preferably 30–100%, most preferably 40–90%.

The weight per square meter of the first textile fabric in the expanded state (in the direction of the fabric) is preferably 50–300 g, more preferably 70–200 g, most preferably 80–120 g.

The definition of the expanded state is according to German standard specification (DIN) 61632, section 6.5.

Consequently, the surface "in the fabric direction expanded state" is characterized as the surface that results by application of a tension of 10 N per 1 cm bandage width after a duration of the force effect of 1 min.

Usually, the first textile fabric is uncolored, i.e. mostly white or weakly colored. However, the possibility also exists to employ a colored first textile fabric that can be obtained according to known textile coloring methods.

The width of the first textile fabric depends on the desired width of the thermoplastic casting material. Typical dimensions for the width are, for example, 5 cm, 7.5 cm, 10 cm or 12.5 cm. However, narrower or broader first textile fabrics can be used without particular limitation.

Although first textile fabrics of different production types can be used, for example, warp knitted, non-woven, woven or knitted materials, warp knitted textile fabrics are particularly preferred.

The size of the pore openings of the first textile fabric results from the thread thickness of the yarn material used and the mesh density (in warp knitted or knitted textile fabrics) or thread density (in woven textile fabrics) of the material. It is approximately 0.5–100 mm$^2$ in the non-expanded stated, preferably 1–40 mm$^2$. The thickness of the first textile fabric in the non-expanded state is preferably 0.3–5 mm, more preferably 1–2 mm.

The expandability in the length-wise and crosswise directions of the first textile fabric, presented above as preferred, can be adjusted in a manner known to the skilled person by selection of the processing parameters in the production of the textile fabric as well as by a suitable selection of the amounts, thickness and relationships of the fibers contained in the textile fabric.

The thermoplastic polymer applied to the first textile fabric is a hot melt adhesive which is stable against hydrolysis and stable in storage that melts at temperatures of 55–90° C., preferably 60–80° C., particularly preferably 60–70° C., and also remains moldable for some time after cooling to below the melting point. In order that the thermoplastic polymer in a thermoplastic casting material is useable under normal application conditions, it must have a temperature resistance to 50° C., preferably to 55° C. i.e. a substantial softening or a decomposition of the plastic cannot occur at these temperatures.

Preferably, the thermoplastic polymer has a melt flow index (125° C.) of 0.5–200 G/10 min., more preferably 6–40 g/10 min., most preferably 12–25 g/10 min, whereby the determination of the melt flow index occurs according to DIN ISO 1133 at a test temperature of 125° C. and a nominal load of 325 g.

The hardening time after heating to or above the melting temperature depends on the attained temperature and the cooling rate and is in general 1–15 min, preferably 2–10 min., particularly preferred 3–8 min.

Suitable thermoplastic polymers with the above mentioned properties are, for example, polyester, polyurethane, polyvinyl acetate or the synthetic polymers disclosed in previously mentioned U.S. Pat. No. 4,143,655 as well, preferably linear saturated polyester compounds. An example for such a polyester is the commercially available polycaprolactone CAPA 640 (manufacturer: Solvay Interox, Warrington, GB).

Aside from the thermoplastic polymers, the thermoplastic polymer can contain, if needed, further adjuvants and additives such as, for example, color pigments, stabilizers, softeners, resins, tackifiers, UV filters, fillers and antioxidation agents.

Mixtures of different polymer compounds can also be used as thermoplastic polymers as long as these are mixable with each other and the obtained mixture has the properties described above.

Furthermore, thermoplastic polymers that have a certain residual flexibility in the hardened state instead of being completely hard can also be used.

Examples for this are ethylene acrylic acid ester copolymers, ethyl vinyl acetate copolymers and polyurethanes.

Casting materials can be obtained by using such thermoplastic polymers that do not cause the complete immobilization of the part of the body provided with the bandage produced therefrom, but merely a semi-rigid immobilization that allows controlled movement and functional loading of the affected part of the body.

The at least one second textile fabric according to the invention is a warp knitted, woven or knitted material or a non-woven material, preferably a warp knitted material.

Preferably, the second textile fabric according to the invention is expandable, particularly preferred elastic, in the length-wise and crosswise direction. In this connection, the length-wise direction characterizes the machine-direction of the fabric and the crosswise direction characterizes the direction perpendicular to this that defines the width of the second textile fabric.

The fiber and/or thread material used for the second textile fabric according to the invention can be of any nature as long as adhesion of neighboring layers of the thermoplastic casting material according to the invention is substantially prevented, even when the thermoplastic polymer is heated to or above its melting point.

Synthetic, regenerated and natural fibers and/or threads as well as mixtures thereof can be used as fiber and/or thread materials. For attaining the particularly advantageous elastic second textile fabric, this is produced from mixtures of elastic and inelastic yarns.

Natural, synthetic as well as inorganic materials such as, for example, glass fibers or carbon fibers of different fiber and/or thread thickness are suitable as non-elastic fibers and/or threads for the second textile fabric according to the invention, preferably cotton or viscose fibers or threads. These can be alternatively used in combination with other synthetic fibers and/or threads such as, for example, polyacrylic, polyamide, aramide, polyester, polyolefins.

Elastic thread elements for the preferably elastic second textile fabric are, for example, yarns of elastodiene, elastane/polyurethane, thermoplastic elastomers, texturized synthetic yarns, highly twisted single threads or highly twisted double threads made from cotton or viscose fibers.

Preferred materials are elastic second textile fabrics of viscose or cotton in mixtures with elastic polyamide or polyurethane threads. Elastic second textile fabrics of viscose and polyamide are particularly preferred.

In one particularly preferred embodiment according to the invention, a second textile fabric is employed that has two sides with different affinity for (compatibility with) the thermoplastic polymer as a result of the fiber materials contained therein and their manner of production. On the one hand, such a second textile fabric can be easily applied with the side that has a high affinity for the thermoplastic polymer to the composite of the first textile fabric and the thermoplastic polymer. On the other hand, a particularly effective prevention of adhesion of neighboring layers of the casting material is brought about as a result of the external side with lower affinity.

The different affinity (compatibility) of the second textile fabric to (with) the thermoplastic polymer can also be brought about by suitable coatings of one or both textile fabric sides. Possible coasting agents for this are, for example, paraffins, waxes, oleophobizing agents or hydrophobizing agents.

The preferred elastic second textile fabric according to the invention has a length-wise expandability of preferably 30–200%, more preferably 60–160%, most preferably 80–130%.

The preferred crosswise expandability is 10–120%, more preferably 30–100%, most preferably 40–90%.

The second textile fabric can have the same width as the first textile fabric contained in the thermoplastic casting material or can have a smaller width than the first textile fabric as long as the adhesion-preventing properties of the second textile fabric are not negatively influenced by this.

The weight per square meter of the second textile fabric according to the invention in the expanded state is preferably 10–80 g, more preferably 15–60 g, most preferably 20–40 g, whereby the expanded stated is defined as described above for the first textile fabric.

Preferred is a second textile fabric that represents a textile material with open-meshed structure; particularly preferred is a warp knitted textile material.

The size of the pore openings of the second textile fabric results, as described for the first textile fabric, from the thread and/or fiber thickness of the materials used and the mesh or thread and/or fiber density of the material.

The pore size in the non-expanded state is approximately 0.1–100 mm$^2$, preferably 1–40 mm$^2$, more preferably 1.5–10 mm$^2$.

The thickness of the second textile fabric is preferably 0.2–5 mm, more preferably 0.5–2 mm, particularly preferably 0.6–0.8 mm.

The thermoplastic casting material according to the invention encompasses the first textile fabric, a thermoplastic polymer applied to the first textile fabric and a second textile fabric applied to this composite and strongly adhering thereto.

Preferably, the thermoplastic polymer is applied on the first textile fabric in melted form, whereby a coating or impregnation is achieved. This manner of application can be carried out in a manner known to the skilled person such that either the entire fiber surface of the first textile fabric is covered with the plastic or an open-meshed coating is obtained.

Furthermore, it is possible to introduce the thermoplastic polymer as a solid film between the first and second textile fabric, whereby a casting material of unbound layers is obtained to begin with. Upon heating of the casting material, the film melts from the thermoplastic polymer and bonds with the first and the second textile fabric to a composite material.

It is equally possible to apply the plastic according to a powder scattering method in which the thermoplastic polymer is spread, preferably as a powder, on the first textile fabric and then this is melted in an oven.

The amount of thermoplastic polymer applied to the first textile fabric is variable and can adjusted to obtain different strengths of the casts to be produced from the thermoplastic casting materials. Preferably, the spread amount in the expanded state of the first textile fabric is 100–500 g/m$^2$, more preferably 200–450 g/m$^2$, most preferably 250–400 g/m$^2$, wherein the expanded state is as defined above.

The portion of the thermoplastic polymer in the casting material according to the invention is preferably 30–95% by weight, more preferably 50–90% by weight, most preferably 60–80% by weight.

The thermoplastic casting material according to the invention is preferably expandable in the length-wise and crosswise direction above the melting point of the thermoplastic polymer. The expandability is influenced by the properties of the first textile fabric and the second textile fabric and can be controlled and adjusted by suitable selection of these components.

The length-wise expandability (as defined above) is preferably 30–120%, more preferably 50–110%, most preferably 60–100%.

The crosswise expandability (as defined above) is preferably 20–120%, more preferably 30–100%, most preferably 40–90%.

The thermoplastic casting material according to the invention is preferably present in roll form, i.e. the fabric material is rolled up and packaged for storage and can be heated in the rolled up state before use. The heated material can then be comfortably unrolled at a suitable rate to produce a bandage and the individual layers are adhered by pressing against each other.

The method according to the invention for the production of the thermoplastic casting material according to the invention encompasses the application of the thermoplastic polymer to the first textile fabric and the subsequent application of at least one second textile fabric according to the invention to the first textile fabric provided with the thermoplastic polymer.

In one embodiment, the first textile fabric, in so far as it is a expandable first textile fabric, is at first coated or impregnated with the thermoplastic polymer in the expanded state at a temperature at which the thermoplastic polymer can be applied to the support material in melted form.

The applicable temperature range lies between the melting temperature of the thermoplastic polymer used and a temperature at which the thermoplastic polymer is not too highly fluid and decomposition does not arise. Temperatures in the range of 70 to 150° C. are preferred, 80 to 120° C. are further preferred, particularly preferred 90 to 110° C.

The impregnation or coating step described above can be carried out with customary devices that can be typically used for the impregnation of textile materials with synthetic polymers.

Subsequently, the at least one second textile fabric according to the invention is applied to the composite of the thermoplastic polymer and the first textile fabric. Preferably, this takes place at a temperature that lies at the melting temperature of the thermoplastic polymer or lies above this such that the second textile fabric is partially pressed into the synthetic polymer by light contact and is held fast thereby after its hardening.

Thus, the second textile fabric can be applied directly subsequent to the impregnation or coating step before the thermoplastic polymer is completely hardened. However, it is also possible to heat the previously cooled impregnated material anew to a temperature above the melting point of the thermoplastic polymer and to then apply the second textile fabric.

Furthermore, it is possible to place the second textile fabric at room temperature on the composite of thermoplastic polymer and the first textile fabric. The bonding to each other then occurs with melting of the synthetic polymer during the use of the casting material.

As an alternative to this, the second textile fabric according to the invention can be applied with a suitable adhesive to the composite of thermoplastic polymer and the first textile fabric. In this connection, the adhesive is to be selected such that detachment of the second textile fabric from the composite does not occur when the thermoplastic casting material according to the invention is heated before use and such that the adhesive does not display a disadvantageous effect on the properties of the second textile fabric. Suitable adhesives for the fixing of the separation layer material to the impregnated support material are, for example, hot-melt adhesives whose melting temperature lies above the temperatures to which the casting material is heated in use.

In a further embodiment of the method according to the invention, the first textile fabric, a film of a thermoplastic polymer and the at least one second textile fabric are superimposed in this order and further processed to a suitable layer form, preferably to a casting material in roll form.

The thermoplastic casting material according to the invention can be used in a versatile manner for the production of bandages for the support or immobilization of parts of the humans or animal body. It is simple and inexpensive to produce and is nearly unlimitedly stable in storage without the necessity of having a hermetically sealed package.

Upon use, the adhesion-preventing effect of the casting material according to the invention is maintained up until the immediate time of application to the part of the body to be provided with the bandage. As a result, a very good unwinding capability of the casting material is ensured even with strong squeezing out of the residual water after heating. On the other hand, the second textile fabric remaining in the bandage does not cause any disadvantageous negative effect of the adhesion of neighboring casting material layers in the applied bandage and leads, at the same time, to an increased stability as well as to an improvement of the air permeability of the resulting bandage.

Since the second textile fabric remains in the casting material, the material is very easy to handle. Furthermore, the outer side of the resulting bandage obtains a textile character as a result of the second textile fabric being oriented to the outside when applying the bandage, whereby the wearing comfort is considerably increased in comparison to previously known casting materials based on polymers.

In the following, the present invention is further illustrated by means of concrete examples.

EXAMPLE 1

First Textile Fabric

By using a 15 gauge narrow warp knitting machine (supplier; Comez SpA, Cilavegna PV, Italy) with 3 bars, and open-meshed textile fabric was produced.
Bar 1: 16.7 tex f48x1 texturizes polyester (elastic yarn)
Bar 2: 55 tex f96x1 polyester (multifilament yarn)
Bar 3: 8 tex polyurethane/elastane (Dorlastan-supplier: GVW Veredelungswerke GmbH, Goch, Germany) intermingled with 7.8 tex f34x1 polyamide (elastic yarn).
The chain link numbers were:
Bar 1: 2.1-2.1
Bar 2: 1.4-4.1
Bar 3: 1.2-2.1
Number of ends:
Bar 1: 61
Bar 2: 59
Bar 3: 61

The elastic thread of bar 3 was supplied with a tension of 10–13 cN in a pre-stretched condition. The final fabric contained 40 courses per 10 cm when the fabric was stretched according to German standard specification (DIN) 61632 with a tension of 10 N/cm width.

The final width was 10 cm (non-stretched) and the weight per square meter was 108 g (stretched according to DIN 61632). The elongation in the length-wise direction was 45%, in the crosswise direction, 85%.

Thermoplastic Polymer

The commercially available product CAPA 640 (supplier: Solvay Interox, Warrington, GB), a polycaprolactone in granulate form with a melting point of 57° C., was employed
Second Textile Fabric By using the same 15 gauge narrow knitting machine as for the first textile fabric, the second textile fabric was produced in an open, net-like structure. In this case, a 2-bar configuration was used.

Bar 1: 8 tex f17x1 texturized polyamide (elastic yarn)
Bar 2: 17 tex viscose
The chain link numbers were:
Bar 1: 2.1-2.1
Bar 2: 1.9-9.1
Number of ends:
Bar 1: 31
Bar 2: 21

In bar 1, every second needle remains empty; in bar 2, the position was: 1 full-1 empty-1 full-3 empty.

The final fabric contained 30 courses per 10 cm, when the fabric was stretched according to DIN 61632 with a tension of 10 N/cm width.

This fabric was shrunk by using steam with a temperature of 100° C. After the steam treatment, the fabric showed at a width of 9 cm, an elongation in the length-wise direction of 150% (according to DIN 61632) and a weight per square meter of 17 g/m$^2$ (stretched, determined according to DIN 61632. The elongation in the crosswise direction was 35%.

The thermoplastic polymer was melted with a twin-screw extruder LD=15/50) with an in-line heated slot nozzle at a temperature of 120° C. and applied to the first textile fabric while maintaining the open net-like structure and the length and crosswise elongation. Amount applied: 360 g/m$^2$ (stretched, DIN 61632). The first textile fabric coated with the thermoplastic polymer was immediately covered with the second textile fabric while maintaining the expansion. After cooling to room temperature, the obtained thermoplastic casting material was cut into 2.8 m strips and rolled into bandages.

For application, the bandages were heated in a water bath at 70° C. for approximately 5 minutes and used on a patient in the customary manner. The therapeutic utility of the casting material is comparable with the commercially available product Articast S (supplier: Beiersdorf AG, Hamburg, Germany), a cast bandage based on moisture hardening polyurethane systems.

EXAMPLE 2

An open-meshed textile fabric with a weight per square meter of 100 g in the expanded state, a length-wise expandability of 85% and a traverse expandability of 60% was produced on a 18 gauge warp knitting machine (supplier: Mueller, Frick, Switzerland, type Raschelina) with four bars.
Bar 1: 28 tex f48x1 polyester (multifilament yarn)
Bar 2: 55 tex f96x1 polyester (multifilament yarn)
Bar 3: 16 tex polyurethane (supplier: Grapher Meyer, Lustenau, Austria) intermingled with 11 tex f34x1 polyamide (elastic yarn), breaking elongation 277%
Bar 4: 55 tex f96x1 polyester (multifilament yarn)
The chain link numbers were:
Bar 1: 2,0-0,2
Bar 2: 0,6-6,0
Bar 3: 0,1-1,0
Bar 4: 6,1-1,6

In Bar 1-4, every second needle remains empty.

The elastic thread of bar 3 was fed to the knitting machine under an expansion of 130%.

The final fabric contained 24 courses per 10 cm (stretched, DIN 61632) as well as 34 wales per 10 cm (non-stretched). The final width of the first textile fabric was 10 cm (non-stretched).

Thermoplastic Polymer

The commercially available product CAPA 640 (supplier: Solvay Interox, Warrington, GB), a polycaprolactone in granulate form with a melting point of 57° C., was employed.

Second Textile Fabric

A second textile fabric with an open net-like structure and a weight per square meter in the expanded state of 25 g, an elongation in the length-wise direction of 120% and a elongation in the crosswise direction of 50% was produced on a 14 gauge warp knitting machine with three bars.
Bar 1: 4.4 tex f13x1 polyamide, texturized (elastic yarn)
Bar 2: 17 tex viscose
Bar 3: 17 tex viscose
The chain link numbers were:
Bar 1: 2,0-0,2
Bar 2: 2,2-0,0-0,0-0,0-2,2-2,2
Bar 3: 0,0-4,4-8,8-12,12-8,8-4,4

In bar 1 and 2, every needle was full; in bar 3, the position was: 1 full-1 empty-1 full-1 empty.

The final second fabric contained 60 courses per 10 cm (stretched, DIN 61632) as well as 56 wales per 10 cm (non-stretched). The final width of the first textile fabric was 10 cm (non-stretched).

The expandability was achieved by a treatment of the material with steam. The width of the non-expanded second textile fabric was 10 cm.

The thermoplastic polymer was applied with a hot melt application device comprising a melting tank and a slot nozzle with a temperature of 100° C. to the first textile fabric while maintaining the open net-like structure and the length and crosswise elongation. Applied amount: 310 g/m$^2$ (stretched). The first textile fabric coated with the thermoplastic polymer was immediately covered with the second textile fabric while maintaining the expansion. After cooling to room temperature, the obtained thermoplastic casting material was cut into 2.5 m strips and rolled into bandages.

For application, the bandages were heated in a water bath at 70° C. for 5 minutes and rolled into a 3-layered formed piece. The layer adhesion as well as the strength obtained are comparable with the commercially available product Articast S (supplier: Beiersdorf AG, Hamburg, Germany), a cast bandage based on moisture hardening polyurethane systems.

EXAMPLE 3

An open-meshed textile fabric with a weight per square meter of 93 g in the expanded state, a length-wise expandability of 60% and a crosswise expandability of 80% was produced on a 9 gauge warp knitting machine (supplier: Mueller, Frick, Switzerland, type Raschelina) with two bars.
Bar 1: 16.7 tex f30x1 polyester texturizes (elastic yarn)
Bar 2: 55 tex f96x1 polyester (multifilament yarn)
The chain link numbers were:
Bar 1: 2,0-0,2
Bar 2: 0,0-6,6

In bar 1 and 2, every needle was full.

The final fabric contained 40 courses per 10 cm (stretched, DIN 61632) as well as 43 wales per 10 cm (non-stretched). The width of the non-stretched first textile fabric was 10 cm. The material obtained the expandability through a steam treatment. The width of the first textile fabric was 10 cm.

Thermoplastic Polymer

The commercially available product Unex 4103 (supplier: Dakota Coatings, Neerhonderd, Belguim), a polyurethane with a melting range of 60–70° C. and a temperature resistance up to 50° C., was employed.

Second Textile Fabric

The commercially available product Co-Flex (supplier: Andover Ltd., Salisbury, Mass., USA), a cohesive polyamide non-woven bandage with fine-net structure, having a weight per square meter of 52 g (stretched, DIN 61632), an elongation in the length-wise direction of 160% and an elongation in the crosswise direction of 25%, was employed.

Components of the non-woven bandage:

The non-woven base material of the second textile fabric consisted of polyamide with 44 polyurethane fibers (fiber denier 8.8 tex)/10 cm as an elastic component.

The thermoplastic polymer was sprinkled as a powder in an amount of 310 g/m$^2$ on the expanded first textile fabric with a weight per square meter of 93 g and melted in a hot-air continuous oven.

Subsequently, the second textile fabric was laminated onto the composite of thermoplastic polymer and the first textile fabric. The obtained thermoplastic casting material with a width of 10 cm had an elongation in the length-wise direction of 60% and an elongation in the crosswise direction of 70%.

What is claimed is:

1. Thermoplastic casting material, which is rigid or semi-rigid at temperatures of 50° C., or below and has self-adhesive properties in its softened state, comprising a first textile fabric, a thermoplastic polymer having a melting point of 55–90° C. applied to the first textile fabric and at least one second textile fabric applied to this composite, wherein the thermoplastic polymer is thermoplastic polymer with a melt flow index (125 degrees Celsius) of 0.5–200 g/10 min.

2. Thermoplastic casting material according to claim 1, wherein the first and the at least one second textile fabric are expandable textile fabrics.

3. Casting material according to claim 1, wherein at least one of the first textile fabric and the at least one second textile fabric, comprises an elastic material, selected from threads, fibers and mixtures thereof.

4. Casting material according to claim 1, wherein the length-wise expandability of the casting material is at least 30% at a temperature above the melting point of the thermoplastic polymer and the crosswise expandability is at least 10%.

5. Casting material according to claim 1, wherein at least one of the first textile fabric and the at least one second textile fabric, is a warp knitted fabric, knitted fabric, woven fabric or non-woven fabric.

6. Casting material according to claim 1, wherein the first textile first has a weight per square meter of 50–200 g in the expanded state and the second textile fabric has a weight per square meter of 10–50 g in the expanded state.

7. Casting material according to claim 1, wherein the portion of the thermoplastic polymer in the casting material is 30–95% by weight.

8. Casting material according to claim 1, wherein the second textile fabric has two sides with different affinity for the thermoplastic polymer.

9. Method for the production of a thermoplastic casting material according to claim 1 comprising the following steps:
   a) application of a thermoplastic polymer on a first textile fabric and
   b) application of at least one second textile fabric on the first textile fabric from step a) provided with the thermoplastic polymer.

10. Method according to claim 9 comprising the following further step:
    c) rolling up the material obtained from step b) into a roll-shaped casting material.

11. Casting material according to claim 1, wherein at least one of the first textile fabric and the at least one second textile fabric, is made of a mixture of inelastic and elastic materials, which inelastic and elastic materials are each selected from threads, fibers and mixtures thereof.

12. Casting material according to claim 11, wherein the inelastic material present in the first textile fabric comprises a material selected from cellulose, cotton, viscose, polyacrylic, polyamide, aramide, polyester, polyolefins, glass, carbon and mixtures thereof.

13. Casting material according to claim 11, wherein the inelastic material present in the second textile fabric comprises a material selected from cellulose, cotton, glass or carbon, optionally in combination with other synthetic fibers or threads of polyacrylic, polyamide, aramide, polyester, polyolefins and mixtures thereof.

14. Casting material according to claim 11, wherein the elastic material present in the first and second textile fabric comprises a material selected from elastodiene, thermoplastic elastomers, elastane, texturized synthetic yarns, highly twisted single threads and highly twisted double threads made from cotton or viscose fibers.

* * * * *

UNITED STATES PATENT AND TRADEMARK OFFICE
CERTIFICATE OF CORRECTION

PATENT NO. : 6,358,220 B1
DATED : March 19, 2002
INVENTOR(S) : Gunter Langen et al.

It is certified that error appears in the above-identified patent and that said Letters Patent is hereby corrected as shown below:

Column 12,
Line 32, change "first" to -- fabric --.

Signed and Sealed this

Thirteenth Day of August, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.   : 6,358,220 B1
DATED        : March 19, 2002
INVENTOR(S)  : Gunter Langen et al.

It is certified that error appears in the above-identified patent and that said Letters Patent is hereby corrected as shown below:

<u>Column 12,</u>
Line 45, change "first" to -- fabric --.

This certificate supersedes Certificate of Correction issued August 13, 2002.

Signed and Sealed this

Nineteenth Day of November, 2002

Attest:

Attesting Officer

JAMES E. ROGAN
*Director of the United States Patent and Trademark Office*